United States Patent [19]

Martin

[11] Patent Number: 4,846,183
[45] Date of Patent: Jul. 11, 1989

[54] BLOOD PARAMETER MONITORING APPARATUS AND METHODS

[75] Inventor: Alan D. Martin, Boulder, Colo.

[73] Assignee: The BOC Group, Inc., Montvale, N.J.

[21] Appl. No.: 127,741

[22] Filed: Dec. 2, 1987

[51] Int. Cl.$^4$ .............................................. A61B 5/00
[52] U.S. Cl. ...................................... 128/633; 356/41; 364/413.09
[58] Field of Search .......................... 128/633; 356/41; 364/416

[56] References Cited

U.S. PATENT DOCUMENTS

| 4,167,331 | 9/1979  | Nielsen         | 128/633 |
| 4,407,290 | 10/1983 | Wiber           | 128/633 |
| 4,651,741 | 3/1987  | Passafaro       | 128/633 |
| 4,653,498 | 3/1987  | New, Jr. et al. | 128/633 |
| 4,714,341 | 12/1987 | Homaguri et al. | 128/633 |

FOREIGN PATENT DOCUMENTS 0194105  9/1986  European Pat. Off. ............ 128/633

Primary Examiner—A. Michael Chambers
Attorney, Agent, or Firm—Larry R. Cassett; Roger M. Rathbun

[57] ABSTRACT

A pulse oximeter or plethysmographic device utilizes light varying in intensity at a predetermined carrier frequency. A passive resonant circuit having a resonant frequency substantially equal to the carrier frequency is connected between the photodetector and the first amplifier. The resonant circuit serves to suppress spurious DC and low frequency components such as those due to ambient light and ambient light flicker and also to suppress high frequency interference. Because ambient light signals are suppressed, there is no need for dark current correction or restoration. Suppression of ambient light and other interference upstream of the front end amplifier avoids saturation of the amplifier and permits use of a front end amplifier having high gain.

19 Claims, 2 Drawing Sheets

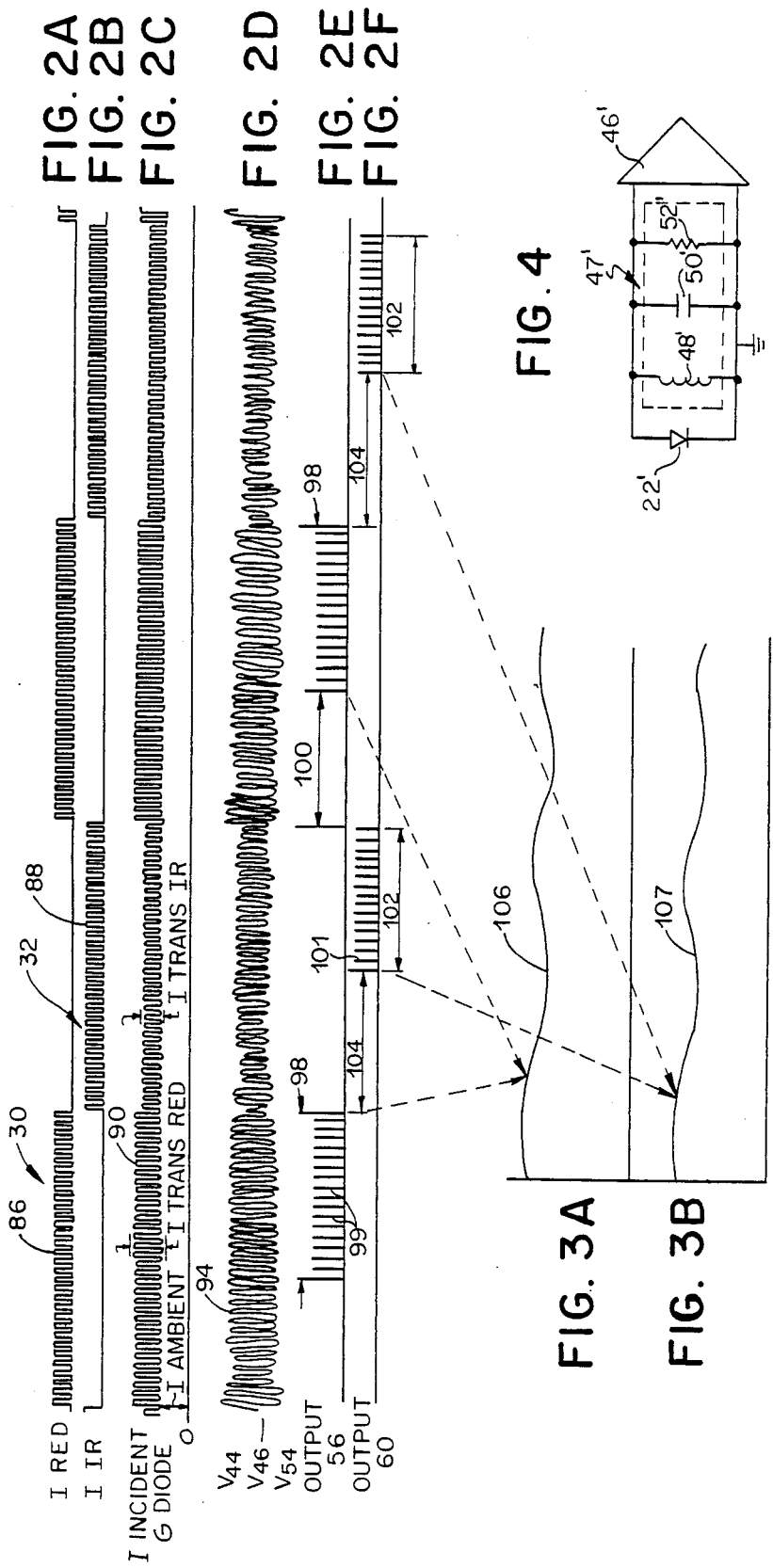

BLOOD PARAMETER MONITORING APPARATUS AND METHODS

BACKGROUND OF THE INVENTION

The present invention relates to apparatus and methods for monitoring one or more parameters of the blood of a living organism.

Certain constituents in the blood affect the absorption of light at various wavelengths by the blood. For example, oxygen in the blood binds to hemoglobin to form oxyhemoglobin. Oxyhemoglobin absorbs light more strongly in the infrared region than in the red region, whereas hemoglobin exhibits the reverse behavior. Therefore, highly oxygenated blood with a high concentration of oxyhemoglobin and a low concentration of hemoglobin will tend to have a high ratio of optical transmissivity in the red region to optical transmissivity in the infrared region. The ratio of transmissivities of the blood at red and infrared wavelengths can be employed as a measure of oxygen saturation.

This principle has been used heretofore in oximeters for monitoring oxygen saturation of the blood in the body of a living organism, as, for example, in patients undergoing surgery. As disclosed in U.S. Pat. No. 4,407,290, oximeters for this purpose may include red light and infrared light emitting diodes together with a photodetector. The diodes and photodetector typically are incorporated in a probe arranged to fit on a body structure such as an earlobe or a fingertip, so that light from the diodes is transmitted through the body structure to the photodetector. The infrared and red light emitting diodes are switched on and off in alternating sequence at a switching frequency far greater than the pulse frequency. The signal produced by the photodetector includes alternating portions representing red and infrared light passing through the body structure. These alternating portions are segregated by sampling devices operating in synchronism with the red/infrared switching, so as to provide separate signals on separate channels representing the red and infrared light transmission of the body structure. After amplification and low-pass filtering to remove signal components at or above the switching frequency, each of the separate signals represents a plot of optical transmissivity of the body structure at a particular wavelength versus time.

Because the volume of blood in the body structure varies with the pulsatile flow of blood in the body, each such signal includes an AC component caused only by optical absorption by the blood and varying at the pulse frequency or heart rate of the organism. Each such signal also includes an invariant or DC component related to other absorption, such as absorption by tissues other than blood in the body structure. According to well known mathematical formulae, set forth in said U.S. Pat. No. 4,407,290, the oxygen saturation in the blood can be derived from the magnitudes of the AC and DC components of these signals.

As also set forth in the '290 patent, the same general arrangement can be employed to monitor constituents of the blood other than oxygen such as carbon dioxide, carbon monoxide (as carboxyhemoglobin) and/or blood glucose, provided that the other constituents have some effect on the optical properties of the blood.

Measurement apparatus and methods of this type have been widely adopted in the medical profession. However, such apparatus and methods have been subject to interference from ambient light falling on the photodetector. The signal processing devices used to recover the AC and DC components after amplification of the photodetector signal have been provided with circuits for cancelling signal components caused by ambient light. Generally, these circuits operate by obtaining a "dark current" signal representing the amplified photodetector signal during intervals when both of the light emitting diodes are off and hence all of the light falling on the photodetector represents ambient light. The dark current signal value can be used to cancel the ambient light component in signals representing infrared and red light.

This approach provides only a partial solution to the ambient light interference problem. The dark current cancellation circuitry adds complexity and cost to the apparatus. Moreover, the ambient light ordinarily flickers at about twice the local power line frequency (100 or 120 Hz), thus introducing a substantial component at these frequencies into the photodetector signal. The low-pass filters must be arranged to suppress these flicker components while passing the AC component at the pulse frequency and also maintaining acceptable limits on phase distortion of the filterd signals. The low-pass filters therefore may require expensive hand-matched components to achieve proper performance.

Moreover, the ambient light signals may saturate the initial or front end amplifier connected to the photodetector. Thus, The signals caused by ambient light may cause the front end amplifier to exceed its maximum rated output, resulting in unpredictable fluctuations in the amplifier output. To prevent saturation of the front end amplifier, its gain may be limited, but this in turn requires higher gain in subsequent stages, more amplification stages or both. Baffles have been used to reduce the amount of ambient light reaching the photodetector and thus prevent saturation. These baffles add further complexity and cost, and are only partially effective.

In addition, interference from sources other than ambient light can saturate the front end amplifier or create spurious signals. In particular, electromagnetic fields from electrosurgical devices or the like may create substantial signals in the photodetector or its leads through capacitive or inductive coupling. The shielding used to protect the photodetector and leads from such interference adds further cost, complexity and bulk.

Accordingly, there have been significant unmet needs heretofore for still further improvements in blood constituent monitoring apparatus such as medical oximeters.

SUMMARY OF THE INVENTION

The present invention provides apparatus and methods which address these needs.

Apparatus according to one aspect of the present invention includes illumination means for emitting light, preferably at a plurality of wavelengths and directing the emitted light through a body structure. Photodetector means are provided for receiving light transmitted from the illumination means through the body structure and producing a photodetector signal representing the intensity of the transmitted light. The illumination means and photodetector means may include, respectively, light emitting diodes and a photoconductor such as a photodiode.

Carrier frequency means are provided for varying the intensity of the light emitted by the illumination means at a carrier frequency. The carrier frequency desirably is far above the pulse frequency of the patient and far above the flicker frequency of the ambient illumination. Because the light emitted by the illumination means and transmitted through the body varies at the carrier frequency, the photodetector signal will also vary at the carrier frequency. The component of the photodetector signal at the carrier frequency will represent light transmitted through the body structure and hence will bear information relating to the optical absorptivity or transmissivity of the body structure at each wavelength emitted by the light emitting means.

Most preferably, modification means are provided for modifying the photodetector signal to increase the ratio of carrier frequency component to other components and thereby provide a modified signal. The modification means preferably attenuates the other components, and may also boost the carrier frequency component. The modification means desirably includes a passive resonant circuit having a resonant frequency substantially matched to the carrier frequency.

Amplification means are provided for amplifying the modified signal and interpretation means are provided for determining a parameter of the blood in the body structure from the amplified signal. The parameter so determined may be the level of a constituent such as oxygen in the blood. The amplification means may include a generally conventional front end amplifier having an input node connected to an output node of the photodetector, whereas the resonant circuit of the modification means may include a capacitor and an inductor connected to the input node of the amplifier so as to shunt signal components at frequencies other than the carrier frequency away from the input node. In some embodiments according to this aspect of the present invention, the interpretation means includes means for separating components of the amplified signal to form separate signals representing the optical transmissivity of the body structure at the different wavelengths, and means for recovering the DC and AC components of these signals to thereby determine the level of the blood constituent.

Photodetector signal components caused by ambient light may be substantially suppressed by the modification means without ever reaching the amplification means or front end amplifier. The front end amplifier therefore is substantially immune to saturation caused by ambient light. The gain of the front end amplifier need not be restricted to avoid such saturation. Requirements for shielding the photodetector from ambient light can be significantly relaxed. Therefore, the probe or photodetector mounting may be simpler, more compact and more convenient. The dark current subtraction or cancellation circuits are not required in the interpretation means, leading to further simplification and cost savings. Because ambient light signals are substantially blocked by the modification means, the lowpass filters in the interpretation means need not be arranged to block ambient light flicker components. The low-pass filters therefore can be simpler than those previously employed.

The modification means or passive resonant circuitry also blocks spurious signals caused by electromagnetic interference. Thus, preferred apparatus according to this aspect of the invention can function effectively even in the presence of relatively "noisy" interfering equipment such as electrosurgical devices. Also, the requirements for electromagnetic interference shielding of the photodetector and associated leads can be significantly relaxed.

The carrier frequency means may be arranged to vary the amplitude of the light of all of the different wavelengths emitted by the illumination means at a single carrier frequency, and the modification means may include resonant circuitry having a single resonant frequency substantially equal to this carrier frequency. In this arrangement, the apparatus may include timing means for actuating the illumination means to emit light of each wavelength at different times according to a predetermined time division schedule. Thus, bursts of light of the different wavelengths may follow one another in alternating sequence at a predetermined switching frequency lower than the carrier frequency but higher than the pulse frequency of the subject. The interpretation means may include means for sampling the amplified signal at the times associated with the different wavelengths and directing the sampled signals accordingly into different signal processing channels. In systems of this nature, the resonant circuit preferably is at least critically damped, and more preferably somewhat overdamped. Therefore, the resonant circuit comes to steady state oscillation at the carrier frequency quickly during each burst of light, allowing use of a relatively high switching frequency.

According to the broadest concepts of the present invention, more than one carrier frequency may be employed. The modification means may be arranged to enhance photodetector signal components of all of these frequencies while suppressing components at other frequencies. Different carrier frequencies may be employed for light of different wavelengths. Light of plural wavelengths may be emitted simultaneously. Preferably, light of all of the different wavelengths is emitted continuously. In this arrangement, the photodetector signal may include components at different carrier frequencies representing transmissivity of the body structure at different wavelengths. The modification means may include separate resonant circuits, each resonant at the carrier frequency associated with a different wavelength. The photodetector signal is fed to these resonant circuits, and the separate modified signal output by each resonant circuit is supplied to a separate signal channel via a separate front end amplifier. Thus, the modification means or resonant circuits in this arrangement serve to separate the signal components associated with the different wavelengths of light as well as to provide the other advantages noted above. In this arrangement, the need for switching, timing and sampling circuitry associated with the time division multiplexing arrangement is eliminated.

Further aspects of the present invention include methods of monitoring blood constituents. In preferrred methods according to this aspect of the invention, light at a plurality of wavelengths is emitted and passed through a body structure, the intensity of the emitted light being varied at a carrier frequency as discussed above. The light passsing through the body structure is detected to provide a photodetector signal having a carrier frequency component bearing information relating to the optical transmissivity of the body structure at the plural wavelengths. The photodetector signal is modified so as to selectively increase the ratio of the carrier frequency component to other components. The modified signal is amplified and the level of the blood constituent is determined from the amplified signal. Methods according to this aspect of the present invention provide advantages similar to those discussed above in connection with the apparatus.

The foregoing and other objects, features and advantages of the present invention will be more fully apparent from the detailed discussion of the preferred embodiments set forth below taken in conjunction with the accompanying drawings.

BRIEF DESCRIPTION OF THE DRAWINGS

FIGS. 2A through 2F are a schematic depictions of certain wave forms occurring during operation of the apparatus depicted in FIG. 1, all on the same time scale.

FIGS. 3A and 3B are depictions of other waveforms occurring during operation of the apparatus depicted in FIG. 1 on a time scale different from that of FIGS. 2A-2F.

FIG. 4 is a fragmentary schematic view of apparatus according to a further embodiment of the invention.

DETAILED DESCRIPTION OF THE PREFERRED EMBODIMENTS

Figure 1:
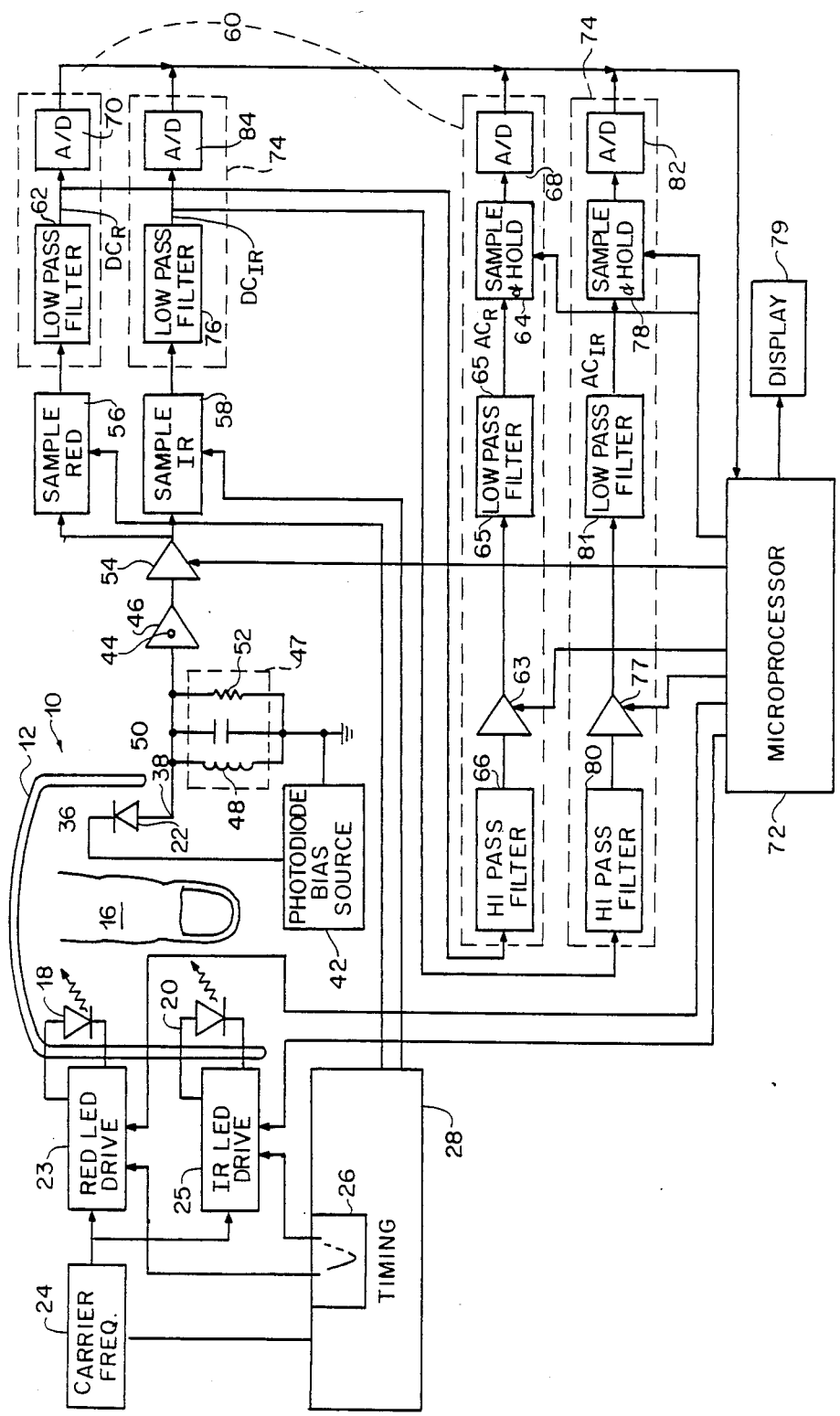
FIG. 1 is a schematic, partially block diagram of apparatus in accordance with one embodiment of the invention.

Apparatus according to one embodiment of the present invention includes a probe 10 incorporating a clip 12 adapted to mount on a body structure such as finger tip 16. A light source including a red light emitting diode or "LED" 18 and infrared LED 20 is mounted to clip 12. A photodiode 22, which in this case is a photoconductive diode is also mounted to clip 12. Clip 12 is arranged so that light from LED's 18 and 20 is directed through the body structure of fingertip 16 towards photodetector 22.

A carrier frequency generator 24 is connected to red LED drive 23 and to infrared LED drive 25, which in turn are connected to LED's 18 and 20 respectively. Generator 24 is arranged to supply power varying in accordance with a square waveform having a predetermined carrier frequency, in this case 19.2 kHz. A master timing unit 28 is arranged to generate a two state square switching wave having a frequency of 300 Hz, or exactly 1/64 of the carrier frequency supplied by carrier frequency generator 24. Timing unit 28 is arranged to actuate a high speed switch 26 and to provide an actuating signal through switch 26 alternately to red LED drive 23 or to infrared LED drive 25 in accordance with the switching wave. Each drive provides power to the associated LED only while that drive receives the actuating signal through switch 26. While each drive is active, it supplies power to the associated LED varying in accordance with the carrier frequency waveform. Thus, red drive 23 and LED 18 are actuated during one-half of the switching waveform whereas infrared drive 25 and LED 20 are actuated during the other half. Carrier frequency generator 24 is also connected to timing unit 28 so that the 19.2 kHz carrier frequency waveform is synchronized with the 300 Hz switching waveform. A cycle of the carrier frequency waveform commences simultaneously with the start of each cyle of the switching waveform.

As drives 23 and 25 and LED's 18 and 20 respond to the driving power from carrier frequency generator 24 in alternating sequence according to the switching waveform from timing unit 28, the LED's will produce alternating bursts of red and infrared light as shown in FIG. 2A and 2B respectively. Curve 30 shows the intensity of red light $I_R$ emitted by LED 18, whereas curve 32 shows the intensity of infrared light $I_{IR}$ emitted by LED 20 on the same time scale. As indicated, bursts 86 of red light alternate with bursts 88 of infrared light, there being one burst of red light and one burst of infrared light within each cyle of the switching waveform. The bursts follow in close sequence, so that a burst of infrared light follows immediately after each burst of red light, and vice versa. Each burst occupies one-half of the 300 Hz switching cycle. Thus, each burst lasts for 1/600 second. Within each burst, the intensity of light varies in accordance with the carrier frequency waveform. As the swtiching frequency of 300 Hz is exactly 1/64 of the carrier frequency, each burst includes 32 cycles of the carrier frequency waveform.

Photodiode 22 has an input node 36 and an output node 38. Input node 36 is connected to a DC voltage bias source 42 so that the photodiode is reverse biased. As the conductance G of photodiode 22 in this reverse bias mode varies with the intensity of light falling on the diode, the voltage at ouput node 38 will also tend to vary in accordance with the amount of light falling on the diode. Output node 38 is connected to the input node 44 of a front end amplifier 46. An inductor 48, capacitor 50 and resistor 52 are connected in parallel with one another between output node 38 and ground so that the inductor, capacitor and resistor cooperatively define a damped inductive/capacitive passive resonant circuit 47 in parallel with the input node of the amplifier.

The output of amplifier 46 is connected to the input of an intermediate amplifier 54, the output of intermediate amplifier 54 in turn being connected to a pair of signal sampling units 56 and 58. Sampling units 56 and 58 are controlled by timing unit 28 so that each sampling unit samples the amplified signal at predetermined times during the switching waveform as further discussed hereinbelow. The samples taken by unit 56 are fed to signal processing channel 60. Channel 60 includes a low-pass filter 62 having a top cutoff frequency of about 10 Hz. The filter is arranged to pass signals below this frequency and to substantially reject signals above this frequency. The top cutoff frequency of filter 62 is well below the 300 Hz switching frequency and hence far below the 19.2 KHz carrier frequency. The output of low-pass filter 62 is connected to an analog to digital converter 70, and also to the input of a high pass filter 66. High pass filter 66 is arranged to attenuate frequencies below about 0.5 Hz and to pass frequencies above about 0.5 Hz. The 0.5 Hz value represents the "corner" frequency of the high pass filter, i.e., the frequency at which the filter provides 3 db attenuation. Frequencies below 0.5 Hz are attenuated to a greater degree. The output of high pass filter 66 is connected to the input of an amplifier 63 referred to herein as a "channel amplifier." The output of channel amplifier 63 is connected to a low pass filter 65 having a corner or 3 db attenuation frequency of 10 Hz. Low pass filter 65 in turn is connected to sample and hold device 64, and device 64 is connected to a further analog to digital converter 68. Converters 68 and 70 are connected to a microprocessor 72.

The output of sampling unit 58 is connected to a second signal processing channel 74. Processing channel 74 is substantially identical to processing channel 60. Thus, channel 74 incorporates a low pass filter 76, high-pass filter 80, channel amplifier 77, low pass filter 81, sample and hold device 78, and analog to digital converters 82 and 84. Each of these components is substantially identical to the corresponding component of first channel 60.

Microprocessor 72 is arranged to compute the oxygen saturation of the blood in finger tip 16 based upon the data input to the microprocessor via the information supplied through the signal channels 60 and 74 as further described hereinbelow. Microprocessor 72 is connected to a display device 79 such as a numeric readout, printer or the like for displaying the computed oxygen saturation. Microprocessor 72 is also arranged to control sample and hold devices 64 and 78. The microprocessor is also arranged to adjust the power output level of each LED drives 23 and 25, to vary the gain of intermediate amplifier 54 and also to vary the gain of each channel amplifier 63 and 77 as discussed below.

In a method according to one embodiment of the present invention, the timing unit 28, carrier generator 24, switch 26, drives 23 and 25 and diodes 18 and 20 are actuated as described above to produce the aforementioned alternating bursts of red and infrared light 86 and 88, varying within each burst at the 19.2 KHz carrier frequency as illustrated by curves 30 and 32 (FIGS. 2A and 2B). The light from diodes 18 and 20 passing through fingertip 16 is attenuated by the tissues in fingertip 16, including the blood present in the blood vessels within the fingertip. As the amount of blood within the fingertip and hence the length of the light path through the blood vessels vary with the patient's pulse cycle, the attenuation of light by the fingertip will also vary in accordance with the pulse cycle. However, this variation occurs at the frequency of the pulse which is below about 5 Hz (300 pulses/min.), and hence far below the 300 Hz switching frequency. Accordingly, the attenuation of the red and the infrared light passing through the fingertip may be regarded as substantially constant during each cycle of the switching waveform or during each burst of red or infrared light.

The intensity $I_{Incident}$ (FIG. 2C) of the light impinging on photodetector 22, as shown by curve 90 (FIG. 2C) will include an ambient component $I_{Ambient}$ and a transmitted component $I_{Trans}$. The transmitted component $I_{Trans}$ represents red or infrared light transmitted from the diodes 18 or 20 to photodetector 22. The magnitude of $I_{Trans}$ will, of course, depend upon the attenuation caused by the fingertip. Also, $I_{Trans}$ will vary in accordance with the output $I_{Red}$ or $I_{IR}$ of whichever LED is operating. Therefore, $I_{Trans}$ and $I_{Incident}$ will vary in accordance with the 19.2 KHz carrier frequency waveform.

In the condition illustrated by FIG. 2C, the attenuation of red light by the fingertip is relatively mild, whereas attenuation of infrared light is more severe. Therefore, during each red burst 86 (FIG. 2A) the magnitude $I_{Trans}$ of the transmitted light, and hence the magnitude of the carrier frequency variation in the incident light will be relatively large. During each infrared burst 88 (FIG. 2B) the magnitude $I_{Trans}$ of the transmitted light and the magnitude of the carrier frequency variation in the incident light will be relatively small. For practical purposes, the response time of photodiode 22 can be taken as zero or instantaneous. The conductance $G_{diode}$ of diode 22 thus varies according to substantially the same curve 90 as does the intensity of the incident light. The amplitude of the variations in the conductance $G_{diode}$ of photodiode 22 at the carrier frequency therefore represents the transmissivity of the fingertip 16 for the particular wavelength being employed. During each red burst 86, the amplitude of these variations in curve 90 represents the transmissivity of the fingertip in the red region, whereas during each infrared burst 88 this amplitude represents the transmissivity in the infrared region. Stated another way, the output from diode 22 appearing at output node 38 has a component at the carrier frequency, and the amplitude of that component indicates the transmissivity at the red or infrared frequency.

The values of inductor 48, capacitor 50 and damping resistor 52 are selected so that the resonant frequency of the circuit incorporating these elements is substantially equal to the carrier frequency, i.e., about 19.2 kHz. Therefore, the resonant circuit tends to reinforce the component of the photodetector signal at the carrier frequency and to attenuate any component of the photodetector signal at frequencies other than the carrier frequency. DC or 100–120 Hz components caused by ambient lighting and other low frequency components in the photodetector signal will be directed away from the input node 44 of amplifier 46 to groud via inductor 48. Components at frequencies above the carrier frequency, such as the high frequency components of electromagnetic interference and the like will be shunted away from the amplifier to ground via capacitor 50.

Resonant circuit 47 does not respond instantaneously to changes in the photodetector ouput signal or changes in the conductance of the diode. Rather, after the start of each burst the resonant circuit comes to equilibrium gradually. As indicated by curve 94, the voltage at the input node 44, and hence the output voltage of front end amplifier 46 and the output voltage of intermediate amplifier 54 as well, all vary according to a sinusoidal waveform at the carrier frequency. Although the same curve 94 is used in FIG. 2D as indicating all of these voltages, the output voltages of the amplifiers have the same waveform but greater amplitudes than the voltage at input node 44. The amplitudes of all of these voltages show a characteristic rising and falling pattern. Towards the end of each burst 86 or 88, the amplitudes of the carrier frequency variations in these voltages are substantially constant, whereas at the beginning of each burst these amplitudes are in transition. During the early portion of burst 88, the amplitudes of amplifier input and output voltages are gradually decaying to the steady state values which prevail at the end of the same burst. During the next succeeding red burst 96, the amplifier input and output voltages gradually increase once again to new steady state value. The value of damping resistor 52 is selected so that the amplifier input and output voltages stabilize at their steady state values during the first half of each burst, i.e., after about sixteen cycles of the carrier frequency waveform or about 1/1200 sec. The amplitudes of the amplifier signals during the first half of each burst are indeterminate values, whereas steady state values during the last half of each burst are directly related to the amplitude of the transmitted light waveform 90 for the burst.

The output signal from amplifier 54 passes to the sampling units 56 and 58. Sampling unit 56 is associated with the red light wavelength. That is, timing unit 28 controls sampling unit 56 so that this unit samples the amplitude of the amplified signal $V_{54}$ during a predetermined interval 98 (FIG. 2E) within each red burst 86 (FIG. 2A). Each sampling interval 98 is delayed by a predetermined delay time 100 following the start of the associated red burst 86, so that each sampling interval 98 corresponds to the second half of the burst. Each sampling interval 98 thus corresponds to the last sixteen oscillations of the carrier frequency waveform within each red burst. Delay time 100 thus is sufficient for resonant circuit 47 to establish substantially steady state oscillations. During each sampling interval 98, unit 56 is actuated by timing unit 28 to sample the amplified signal $V_{54}$ in synchronism with the carrier frequency waveform, at times corresponding to the peaks of the sinusoidal amplified voltage $V_{54}$. Thus a plurality of individual voltage samples 99 are obtained during each sampling interval 98. Sampling unit 58 is likewise actuated by timing unit 28 to sample the amplitude of amplified signal $V_{54}$ during intervals 102 corresponding to the last half of each infrared burst 88. Each such interval 102 is delayed after the start of the associated infrared burst by an appropriate delay time 104, also corresponding to one-half the duration of the burst. Sampling unit 58 likewise obtains a plurality of individual samples 101 during each sampling interval 102.

The output of sampling unit 56 will be a series of voltage spikes corresponding to the transmissivity of the fingertip for red light, whereas the output from sampling unit 58 will be a series of voltage spikes corresponding to the transmissivity of the fingertip for infrared light. Low-pass filter 62 smooths the outputs from sampling unit 56 to provide a substantially continuously varying signal 106 (FIG. 3A) representing the transmissivity of the fingertip in the red region. Signal 106 is depicted in FIG. 3A on a greatly compressed time scale relative to the time scale employed in FIGS. 2A-2F. The oscillations in signal 106 correspond to the patient's pulse cylce, i.e., below 5 Hz and typically about 1-2 Hz. Thus, the samples 99 taken by red wavelength sampling unit 56 during each sampling interval 98 correspond to a single point on curve 106. Low-pass filter 76 smoothes the discrete sample outputs from sampling unit 58 into a substantially similar continuous signal 107 (FIG. 3B) representing the transmissivity of the fingertip in the infrared region.

The continuous signal 106 from filter 62 is fed to analog to digital converter 70. A digital representation of this signal is passed to microprocessor 72. As shown in FIG. 3A, the AC component of signal 106 is small compared to the DC component of this signal. Therefore, each signal from converter 70 approximates the true DC value. Further, microprocessor 72 performs a digital low pass filtering or averaging on the representations captured over a predetermined time so as to derive a more accurate value of the DC component of transmissivity at the red wavelength.

The signal from low pass filter 62 is also delivered to high pass filter 66. The high pass filter blocks the DC component, and delivers only the AC component to channel amplifier 63. After amplification, the AC component is treated by low pass filter 65 to remove residual noise and/or carrier frequency components, and then sampled by sample and hold unit 64. Microprocessor 72 actuates unit 64 to sample the treated AC component at a sampling frequency of about 25-30 Hz. This sampling frequency is substantially faster than the maximum pulse frequency of about 5 Hz, but substantially slower then the switching frequency of 300 Hz. The sampled values are converted to digital representations by converter 68 and supplied to the microprocessor. From this succession of sampled values, the microprocessor computes the AC component of signal 106 and hence the AC component of the red-wavelength transmissivity.

In exactly the same way, the infrared signal channel 74 and microprocessor 72 cooperate to determine the DC and AC components of the infrared transmissivity. All of these values are substantially free of "dark current" or spurious DC components caused by ambient light falling on detector 22, and hence no DC restoration or dark current subtraction circuitry is required.

The microprocessor continually adjusts the power level of LED drives 23 and 25 and the gains of amplifiers 54, 63 and 77 to keep the signal supplied to each analog to digital converter within the operating range of the converter. For example, if the values of the DC component received through converter 70 approach the upper bound of the converter's range, the microprocessor will reduce the power level applied by red LED drive 23. If the value of the red AC component drops below the operating range of converter 68, the microprocessor will increase the gain of channel amplifier 63, and so on. The microprocessor keeps track of these adjustments, and applies appropriate multipliers to the values received from the analog to digital converters so as to compensate for these adjustments. For example, when the gain of amplifier 63 is increased, the microprocessor applies a correspondingly smaller multiplier to the values received from converter 68. In this way, the microprocessor can determine the true values of the AC and DC transmissivity components.

Microprocessor 72 is arranged to calculate the oxygen saturation of the blood within fingertip 16 according to the formula:

$$\text{Oxygen Saturation} = AR^2 + BR + C$$

WHERE:

$$R = \frac{(AC_R/AC_{IR})}{(DC_R/DC_{IR})}$$

$AC_R$ and $DC_R$ are the AC and DC components, respectively, of the red transmissivity signal;

$AC_{IR}$ and $DC_{IR}$ are the AC and DC components respectively of the infrared transmisivity signal; and A, B and C are constants determined by empirical curve fitting in design of the system, against the results of standard blood oxygen determinations.

The oxygen saturation calculated by microprocessor 72 is displayed on display unit 79. As will be appreciated, apparatus in accordance with the present invention may also include other well known features commonly found in oximeters as, for example, testing devices for checking operation of the system and devices for deriving information concerning the presence or absence of a pulse and the pulse rate from one or both of the pulsatile signals provided by channel amplifiers 63 and 77. For example, the microprocessor can be programmed to detect peaks in the AC component of the red transmissivity signal supplied by amplifier 63 by monitoring the sequence of digital representations delivered through analog to digital converter 68. The pulse rate can be determined from the times between successive peaks, whereas the presence or absence of a pulse can be deduced from the occurrence or nonoccurrence of peaks having at least a predetermined magnitude. As used in this disclosure, the term "parameter of the blood" includes information regarding the pulse as well as information regarding the level of a constituent such as oxygen in the blood. Where the only parameter of the blood to be monitored is the pulse, only one wavelength need be employed. Apparatus for this purpose may include only one LED for one wavelength, and may also include only one signal processing channel and only one LED drive.

The carrier frequency or frequencies utilized in systems according to this aspect of the invention should desirably be well above the fundamental flicker frequencies of the ambient lighting and yet below the principal electromagnetic interference frequencies emitted by electrosurgery equipment and other equipment expected to be used with the oximeter. Carrier frequencies in the range of about 4 kHz to about 30 kHz are preferred, carrier frequencies between about 12 and about 24 kHz being more preferred.

Substantially the same method can be employed to monitor blood constituents other than oxygen saturation, provided that variations in the constituent to be measured cause variations in the optical transmissivity of the blood at different wavelengths. The above noted formula can be generalized to constituents other than oxygen saturation and to measurement of more than one constituent using more than two different wavelengths as set forth in the aforementioned U.S. Pat. No. 4,407,290, the disclosure of which is hereby incorporated by reference herein. As also disclosed in the '290 patent, DC normalization techniques may be employed.

FIG. 4 illustrates a portion of further apparatus according to the invention. In this apparatus, front end amplifier 46' has positive and negative input terminals. The resonant circuit 47' again includes an inductor 48', capacitor 50' and damping resistor 52'. However, in this embodiment, the resonant circuit is connected in parallel with the photodetector or photodiode 22' across the positive and negative input terminals of the amplifier. Photodiode 22' is not biased, and operates in a photoamperic mode at frequencies other than the carrier frequency. At the carrier frequency the photodiode operates in the photovoltaic mode and the resulting voltage is amplified by amplifier 46'. In this arrangement as well, the inductor 48' and capacitor 50' serve to attenuate signal components from diode 22' at frequencies other than the carrier frequency. Damping resistor 52' may include a discrete resistor, the input impedance of amplifier 46 or both.

Substantially the same method can be employed to monitor blood constituents other than oxygen saturation, provided that variations in the constituent to be measured cause variations in the optical transmissivity of the blood at different wavelengths. The above noted formula can be generalized to constituents other than oxygen saturation and to measurement of more than one constituent using more than two different wavelengths as set forth in the aforementioned U.S. Pat. No. 4,407,290, the disclosure of which is hereby incorporated by reference herein. As also disclosed in the '290 patent, DC normaliation techniques may be employed.

FIG. 4 illustrates a portion of further apparatus according to the invention. In this apparatus, front end amplifier 46' has positive and negative input terminals. The resonant circuit 47' again includes an inductor 48', capacitor 50' and damping resistor 52'. However, in this embodiment, the resonant circuit is connected in parallel with the photodetector or photodiode 22' across the positive and negative input terminals of the amplifier. Photodiode 22' is not biased, and operates in a photoamperic mode at frequencies other than the carrier frequency. At the carrier frequency the photodiode operates in the photovoltaic mode and the resulting voltage is amplified by amplifier 46'. In this arrangement as well, the inductor 48' and capacitor 50' serve to attenuate signal components from diode 22' at frequencies other than the carrier frequency. Damping resistor 52' may include a discrete resistor, the input impedance of amplifier 46 or both.

In the embodiments discussed above, the carrier frequency signal, and hence the curves of amplitude versus time for power applied to the LED's and for light emitted by the LED's, have square waveforms. Square waveforms are easy to generate with simple circuitry incorporated in typical digital devices. A square waveform, however, includes significant components at frequencies other than the fundamental frequency of the waveform. Therefore, the square waveforms of the power applied to the LED's and the light emitted by the LED's include significant components at harmonics of the carrier frequency. These harmonic components are effectively blocked by the resonant circuit and hence contribute nothing to the useful carrier frequency signal delivered to the front end amplifer 46. However, these harmonic components are included in the total power dissipated in in the LED's and also contribute to the power radiated as light from the LED's into the patient's body.

The total power which can be applied to the LED's may be limited by the heat dissipation capacity of the LED's. Also, the power applied to the LED's may be limited by the need to limit light radiation into the patient's body, as where the patient is a neonate or other individual whose skin is extraordinarily sensitive.

Where limits on the power applied to the LED's pose a problem, this problem can be alleviated by using a carrier frequency waveform which better approximates a sinusoid. Thus, the carrier frequency waveform and the waveforms of the power applied to the LED's and the light emitted by the LED's may be sinusoidal, which essentially eliminates the useless components at the harmonics included in the square waveform. Alternately, these waveforms may be triangular. The triangular waveform has a significantly lower content of harmonics than does the square waveform. Conventional waveform generation circuitry, well known to those skilled in the art, may be used to generate either the sinusoidal or triangular waveforms, and such conventional circuitry can be incorporated in the carrier frequency generator or in the LED drives. Alternately, the harmonics incorporated in a square or other waveform generated by the LED drives can be blocked by an inductive-capacitive resonant circuit interposed between each LED drive and the associated LED. Preferably, any such additional resonant circuit would be damped.

In the embodiments discussed above, bursts of red and infrared light are provided in alternating sequence with each burst following immediately after the preceding burst to provide substantially continuous illumination. In a further embodiment, the timing means may be arranged to deactivate both the red and infrared LED's so as to provide dark intervals interspersed in the sequence of red and infrared bursts. Appropriate means may be provided for sampling the signal from passive resonant circuit 47 (FIG. 1) as by sampling the amplified signals from intermediate amplifier 54. Desirably, any such dark interval sampling is delayed until after lapse of a suitable delay time from the start of the dark interval. The delay time is selected so that the resonant circuit comes substantially to equilibrium before the dark interval samples are taken. In this equilibrium condition, the modified photodetector signal provided by the resonant circuit consists entirely of interference components within the pass band of the resonant circuit. The microprocessor may be arranged to test the sampled signals and provide an error message on the display unit if the sampled signals during the dark intervals exceed a predetermined threshold. This error condition will occur in the presence of interference, such as radio frequency interference from electrosurgical devices at the carrier frequency. The dark intervals need not be provided on every cycle of the switching waveform. Rather, the time between successive dark intervals need only be short enough to provide the error signal promptly when interference occurs.

As numerous variations and combinations of the features described above can be utilized without departing from the present invention, the foregoing description of the preferred embodiments should be taken by way of illustration rather than by way of limitation of the invention as set forth in the claims.

I claim:

1. Apparatus for monitoring a parameter of the blood within a body structure comprising:
    (a) illumination means for emitting light at at least one wavelength and directing the emitted light through said body structure;
    (b) photodetector means for detecting light from said illumination means transmitted through said body structure and producing at least one photodetector signal representing the intensity of said detected light;
    (c) carrier frequency means for varying the amplitude of the light emitted by said illumination means at at least one carrier frequency whereby said at least one photodetector signal will include at least one component at said at least one carrier frequency bearing information relating to the optical transmissivity of said body structure at said at least one wavelength;
    (d) modification means for modifying said at least one photodetector signal by passing and attenuating components of said at least one photodetector signal dependent upon their respective frequencies so as to increase the ratio of said at least one carrier frequency component relative to other components and thereby provide at least one modifed signal;
    (e) amplification means for amplifying each said modified signal to provide at least one amplified signal; and
    (f) interpretation means for determining said parameter of the blood in said body structure from said at least one amplified signal.

2. Apparatus for monitoring a parameter of the blood within a body structure comprising:
    (a) illumination means for emitting light at at least one wavelength and directing the emitted light through said body structure;
    (b) photodetector means for detecting light from said illumination means transmitted through said body structure and producing at least one photodetector signal representing the intensity of said detected light;
    (c) carrier frequency means for varying the amplitude of the light emitted by said illumination means at at least one carrier frequency whereby said at least one photodetector signal will include at least one component at said at least one carrier frequency bearing information relating to the optical transmissivity of said body structure at said at least one wavelength;
    (d) modification means for modifying said at least one photodetector signal to increase the ratio of said at least one carrier frequency component relative to other components and thereby provide at least one modified signal;
    (e) amplification means for amplifying each said modified signal to provide at least one amplified signal; and
    (f) interpretation means for determining said parameter of the blood in said body structure from said at least one amplified signal, said modification means including at least one passive resonant circuit having a resonant frequency substantially equal to each said carrier frequency.

3. Apparatus as claimed in claim 2, wherein said illumination means includes means for emitting light at a plurality of wavelengths and said interpretation means includes means for determining the level of a constituent of the blood.

4. Apparatus as claimed in claim 3 wherein said carrier frequency means includes means for varying the amplitude of light at all of said plurality of wavelengths emitted by said illumination means at a single carrier frequency, said modification means includes a single passive resonant circuit having a resonant frequency substantially equal to said single carrier frequency, said amplification means includes means for amplifying said modified signal from said single resonant circuit to provide a single amplified signal.

5. Apparatus as claimed in claim 4 further comprising timing means for actuating said illumination means to emit light of each of said plurality of wavelengths at different times according to a predetermined time division schedule so that different times are associated with different wavelengths, said interpretation means including means for recovering information relating to the optical transmissivity of said body structure at each said wavelength from those portions of said amplified signal occurring during the times associated with that wavelength.

6. Apparatus as claimed in claim 5 wherein said single resonant circuit is damped.

7. Apparatus as claimed in claim 6 wherein said timing means includes means for providing bursts of light having said different wavelengths in alternating sequence at a predetermined switching frequency lower than said carrier frequency and wherein said interpretation means includes means for rejecting portions of said amplified signal occurring during the first portion of each such burst.

8. Apparatus as claimed in claim 7 wherein said timing means is arranged to provide said bursts in immediate succession so that a burst of one wavelength follows immediately after a burst of another wavelength.

9. Apparatus as claimed in claim 8 wherein said means for rejecting includes means for sampling said amplified signal during each said burst from said illumination means only after a predetermined delay time has elapsed after the start of the burst, to provide a sampled signal, said interpretation means including means for recovering said information from said sampled signal.

10. Apparatus as claimed in claim 9 wherein said means for recovering information from said sampled signal includes separate signal processing channels associated with each of said wavelengths, said sampling means including means for directing samples of said amplified signal taken during each said burst to the channel associated with the wavelength of such burst.

11. Apparatus as claimed in claim 10 wherein said sampling means includes separate means for sampling said amplified signal during bursts of each said wavelength.

12. Apparatus as claimed in claim 10 wherein each said signal processing channel includes low-pass filter means for eliminating components at and above said switching frequency from the sampled signal in such channel to provide a filtered signal.

13. Apparatus as claimd in claim 12 wherein said interpretation means includes means for capturing the DC and AC components in said filtered signal in each said channel and interpreting said DC and AC components as the DC and AC components respectively, of the transmissivity of said body structure associated with that channel.

14. Apparatus as claimed in claim 2, wherein said photodetector means includes a photoelectric element having an output node connected to said amplification means and said at least one passive resonant circuit includes an inductor and a capacitor connected in parallel to said output node.

15. Apparatus as claimed in claim 14 wherein said photoelectric element includes a photoconductive diode.

16. Apparatus as claimed in claim 15 wherein further comprising bias means for supplying a bias voltage to said photoconductor.

17. A method of monitoring a parameter of the blood within a body structure comprising the steps of:
    (a) emitting light at at least one wavelength while varying the amplitude of the emitted light at at least one carrier frequency and directing the emitted light through the body sturcture;
    (b) detecting light transmitted through the body structure and producing at least one photodetector signal representative of the detected light and having at least one component at each said carrier frequency;
    (c) modifying said at least one photodetector signal by passing and attenuating components of said at least one photodetector signal depending upon their respective frequencies so as to increase the ratio of said at least one carrier frequency component to other components and thereby provide at least one modified signal;
    (d) amplifying said at least one modified signal to provide at least one amplified signal; and
    (e) determining said parameter from said at least one amplified signal.

18. A method of monitoring a parameter of the blood within a body structure comprising the steps of:
    (a) emitting light at at least one wavelength while varying the amplitude of the emitted light at at least one carrier frequency and directing the emitted light through the body structure;
    (b) detecting light transmitted through the body structure and producing at least one photodetector signal representative of the detected light and having at least one component at each said carrier frequency;
    (c) modifying said at least one photodetector signal to increase the ratio of said at least one carrier frequency component to other components and thereby provide at least one modified signal;
    (d) amplifying said at least one modified signal to provide at least one amplified signal; and
    (e) determining said parameter from said at least one amplified signal, said amplifying step including the step of passing said photodetector signal to an input node of an amplifier, and said attenuating step includes the step of maintaining a passive circuit resonant at said at least one carrier frequency in parallel with said amplifier input node.

19. A method as claimed in claim 17 wherein said parameter is the level of a constituent in the blood and said light emitting step includes the step of emitting light at a plurality of wavelengths.

* * * * *